(12) United States Patent  
Soltanpour (10) Patent No.: US 7,780,623 B2
(45) Date of Patent: Aug. 24, 2010

(54) IMPLANTABLE PUMP APPARATUSES (76) Inventor: David P. Soltanpour, 5 Lindsley Dr., Larchmont, NY (US) 10538

( * ) Notice: Subject to any disclaimer, the term of this patent is extended or adjusted under 35 U.S.C. 154(b) by 355 days.

(21) Appl. No.: 11/261,739

(22) Filed: Oct. 31, 2005

(65) Prior Publication Data

US 2007/0106199 A1 May 10, 2007

Related U.S. Application Data

(63) Continuation-in-part of application No. 10/733,090, filed on Dec. 12, 2003, now abandoned, which is a continuation-in-part of application No. 09/841,191, filed on Apr. 25, 2001, now Pat. No. 6,682,500, which is a continuation-in-part of application No. 09/586,962, filed on Jun. 5, 2000, now Pat. No. 6,589,198, which is a continuation-in-part of application No. 09/015,759, filed on Jan. 29, 1998, now Pat. No. 6,168,575.

(51) Int. Cl.
*A61M 5/00* (2006.01)
(52) U.S. Cl. .......................... 604/9; 604/151
(58) Field of Classification Search .............. 604/8, 604/9, 6.16, 119, 151, 890.1; 623/14.13, 623/3.12, 23.68
See application file for complete search history.

(56) References Cited

U.S. PATENT DOCUMENTS 5,171,213 A * 12/1992 Price, Jr. ..................... 604/9
6,589,198 B1 * 7/2003 Soltanpour et al. .......... 604/9

* cited by examiner

*Primary Examiner*—Leslie R Deak
(74) *Attorney, Agent, or Firm*—Alfred F. Hoyte, Jr.

(57) ABSTRACT

An implantable, miniature pump assembly having a flexible elastic bladder actuating assembly. The bladder, in the non-flexed state, has an elongated, substantially rectangular profile, with a predetermined internal volume or capacity. Influent and effluent conduits extend in opposite directions from respective end portions of the bladder. Each of the conduits include one way valves disposed therein to limit fluid flow to a single direction into and through the bladder. Contraction and expansion of the bladder by means of energy harvested from the dynamic environment in which it is implanted in response to ambient random dynamic motion creates alternating pressure and vacuum within the bladder, alternately drawing fluid into the bladder through the influent conduit, and forcing fluid from the bladder via the effluent conduit. The bladder pump assembly harvests its operational energy from the random dynamic motion of the surrounding organs and tissues and therefore does not require an internal or external power source.

5 Claims, 12 Drawing Sheets

Fig. 14

IMPLANTABLE PUMP APPARATUSES

CROSS REFERENCE TO RELATED APPLICATIONS

This application is a continuation in part of application Ser. No. 10/733,090, filed on Dec. 12, 2003 now abandoned; which is a continuation in part of application Ser. No. 09/841,191, filed on Apr. 25, 2001, now U.S. Pat. No. 6,682,500; which is a continuation in part of application Ser. No. 09/586,962, filed on Jun. 5, 2000, now U.S. Pat. No. 6,589,198, which is a continuation in part of application Ser. No. 09/015,759, filed on Jan. 29, 1998, now U.S. Pat. No. 6,168,575.

BACKGROUND OF THE INVENTION

1. Field of the Invention

The present invention relates to pump assemblies. More specifically, it relates to self-powered microminiature bladder pumps which may be used as bio-compatible medical implants for controlling diseases such as glaucoma and hydrocephalus, and to effect drug delivery.

2. Description of the Prior Art

Mechanical and electro-mechanical medical implants are well known, and, depending upon the type, have met with varying success rates. One problem with these devices is the lack of a reliable, long term power source. Ideally, the power source should last for the life of the implant, as many of these implants require invasive procedures both to install and maintain. Indeed, an external power source is virtually impossible in many situations, making the use of internal, self-contained power sources highly preferable.

One use for mechanical implants is the treatment of glaucoma. Glaucoma is a common eye disease which is caused by excessive ocular pressure in the anterior chamber of the eyeball. Many devices and techniques have been devised in order to control this pressure. The devices fall generally into two types; passive devices such as a simple tubular shunt or similar device which drains aqueous humor from the anterior chamber, and active devices which have means for controllably draining ocular pressure by pumping out a small amount of aqueous humor, the systems typically using check valves or similar mechanical devices to regulate pump action. While these systems are somewhat effective, they tend to suffer from the drawback in that they are unreliable or require frequent maintenance which always involves a fairly invasive procedure. Failure to properly maintain the devices can result in long term damage to surrounding tissue especially in the case of pumps used to control glaucoma. Power sources for these implantable pumps have to be either implantable batteries that need to be replaced after a while or transcutaneously charged every once in a while or inductive energy sources which tend to be cumbersome because an inductive energy receiving armature needs to implanted alongside with them and an inductive energy source needs to be brought close to them to induce current and subsequently energize the device.

U.S. Pat. No. 5,370,607 issued to Memmen discloses a glaucoma implant device which has a tubular shunt for draining fluid from the eye.

U.S. Pat. No. 4,911,616 issued to Laumann, Jr. discloses a microminiature pump which may be used to administer medications in sensitive locations in the body such as the eye. The pump is programmable, but the patent does not disclose which aspects of the pump operation can be controlled.

U.S. Pat. No. 5,062,841 issued to Siegel discloses an insulin pump which can be used to pump insulin directly into the bloodstream in response to blood glucose levels.

U.S. Pat. No. 5,433,701 issued to Rubinstein discusses an active ocular pressure control device which, in one embodiment, includes a pump which is selectively operated in response to a control signal from a pressure sensor.

The present invention contemplates a pumping system which utilizes a flexible, pressure reactive bladder as the primary actuator. The system harvests its operational power from the random dynamic motion of its implantation environment.

SUMMARY OF THE INVENTION

The present invention concerns an implantable, self-powered, miniature pump assembly having a flexible bladder actuator which responds dynamically to changes in the local pressure. The pump is particularly adapted for implantation onto a human eye for controlling intraocular pressure as a treatment for glaucoma, the flexible bladder actuator capable of harvesting energy from the implantation environment. The flexible bladder portion of the assembly, in the non flexed state, has an elongated, substantially rectangular profile, with a predetermined internal volume or capacity. Influent and effluent conduits extend in opposite directions from respective end portions of the assembly. Each of the conduits includes a one way valve disposed therein to limit fluid flow to a single direction into and through the bladder. Expansion of the bladder in response to ambient conditions creates a temporary vacuum within the bladder, drawing fluid into the bladder through the influent conduit, whereas contraction of the bladder forces fluid from the bladder via the effluent conduit. The flexible bladder pump assembly may include a plate attached proximately to the distal end of the bladder for distributing the drained aqueous humor over the sclera of the eye. The bladder of the assembly is positioned under the eyelid with the influent conduit inserted into the anterior chamber of the eye. The bladder portion of the assembly is capable of employing the random motion energy of the eye and the ocular muscles to continuously pump aqueous humor out of the anterior chamber, thus limiting the IOP (Intraocular Pressure).

Accordingly, it is a principal object of the invention to provide a self powered pump assembly employing a flexible bladder as the primary actuator.

It is a major object of this invention to provide a family of implantable pump assemblies for controlling IOP having a common actuator mechanism, the size and shape of the pump and the actuator mechanism selected in accordance with the volume of fluid to be displaced for attaining a desired IOP.

It is another object of this invention to provide a family of implantable pump assemblies having an elastic bladder actuator which is powered solely by environmental disturbances which create local pressure variations.

It is another object of the invention to provide an implantable pump assembly having an elastic bladder actuator having a variable interior volume, the interior volume varying in accordance with local pressure variations.

It is still another object of the invention to provide an improved, biologically implantable pump assembly having a pumping rate which is a function of local pressure conditions.

It is yet another object of the invention to provide an implantable pump assembly having an elastic bladder actuator which can be used to effect hydrocephalus liquid drainage from a swollen brain.

It is another object of the invention to provide an implantable pump assembly having an elastic bladder actuator which can be used to administer drugs.

It is another object of the invention to provide an improved method and apparatus for controlling glaucoma including a micropump having an elastic bladder actuator which is implanted into the anterior chamber of the eye.

It is another object of the invention to provide an improved method and apparatus for controlling glaucoma including a micropump where pump operation is controlled in accordance with the sensed ocular pressure.

It is yet another object of the invention to provide an improved, biologically implantable pump assembly having a draining tube with a relatively wide outlet end to disperse the outflow of fluid.

Finally, it is a general object of the invention to provide improved elements and arrangements thereof in an apparatus for the purposes described which is dependable and fully effective in accomplishing its intended purposes.

These and other objects of the present invention will become readily apparent upon further review of the following specification and drawings.

BRIEF DESCRIPTION OF THE DRAWINGS

Various other objects, features, and attendant advantages of the present invention will become more fully appreciated as the same becomes better understood when considered in conjunction with the accompanying drawings, in which like reference characters designate the same or similar parts throughout the several views, and wherein.

DETAILED DESCRIPTION OF THE PREFERRED EMBODIMENTS

Figure 1:
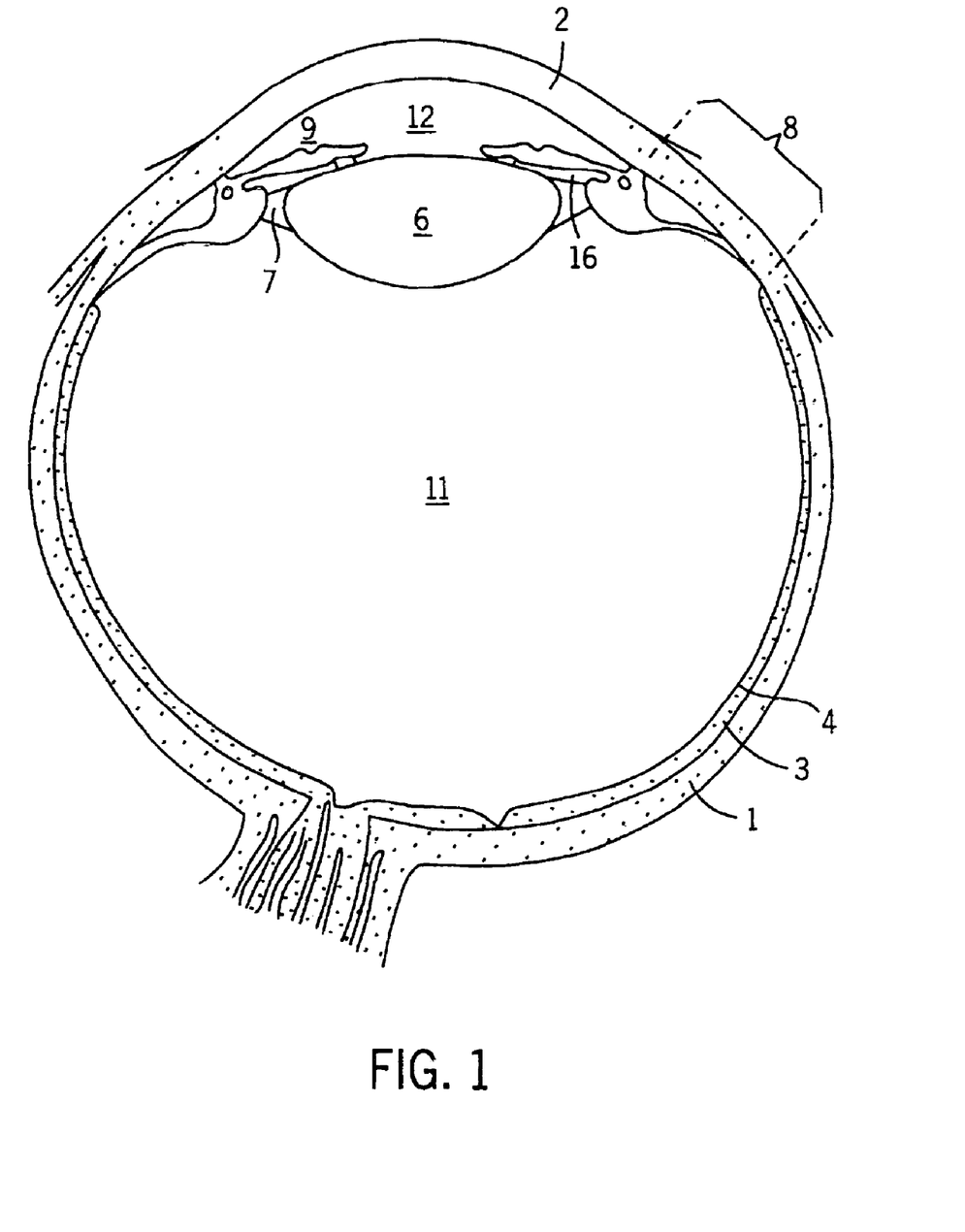
FIG. 1 is a sectional view of a human eye.

The major anatomical structures of the eye are shown in FIG. 1. The eye is surrounded by an outer protective layer, the sclera 1. The anterior portion of the sclera 1, the cornea 2, is modified to allow light rays to enter the eye. The choroid 3 resides within the sclera 1 and comprises vasculature which nourishes most of the structures of the eyeball. The posterior portion of the choroid 3 is lined by the retina 4. The retina 4 is composed of the neural tissue containing the receptor cells that receive and process the incoming light rays.

FIG. 1 also illustrates several other structures of the eye, particularly those areas to be affected by the pump assembly of the invention, generally indicated by the numeral 10. The transparent, biconvex lens 6, one of the refractive media of the eye, is secured by the lens ligament 7 to the ciliary body 8. The ciliary body 8 is the thickened anterior portion of the choroid 3. The iris 9, the "colored" portion of the eye, lies in front of the lens 6 and is composed of circular muscle fibers (not shown) that constrict the pupil and radial muscle fibers (not shown) that dilate the pupil. The relatively large region behind the lens 6 contains the vitreous humor 11, a clear gelatinous material. In contrast, the anterior chamber 12 of the eye contains a clear liquid material called the aqueous humor; the aqueous humor is also referred to as intraocular fluid. As described in more detail below, aqueous humor is produced in the ciliary body/ciliary processes 8. A region exists between the lens 6 and the iris 9, called the posterior chamber 16, that is also filled with aqueous humor.

The normal circulation of aqueous humor through the anterior chamber 12 and posterior chamber 16 against resistance not only satisfies corneal and lenticular metabolism, it also maintains optical clarity and the shape of the eye.

In a normally functioning eye, aqueous humor enters the posterior chamber 16 from the ciliary body/ciliary processes 8 as a consequence of hydrostatic and osmotic gradients between the posterior chamber and the ciliary process vasculature and stroma and active ionic transport across the ciliary epithelium. The aqueous humor then flows around the lens 6 and through the pupil into the anterior chamber 12. The aqueous humor then leaves the eye by passive bulk flow via two pathways leading from the anterior chamber, a detailed discussion of this process is beyond the scope of the present invention. For the purposes of the invention however, it has been recognized that in a normally functioning eye, aqueous humor is continually being produced and drained, and it is the balance between these two processes that regulates the pressure of the intraocular fluid (i.e. the Intraocular Pressure or IOP). As previously indicated, glaucoma is characterized by elevated intraocular pressure.

Referring now to FIGS. 2A-8, the pump assembly 10, is shown connected to a drainage distribution plate 70. The assembly 10 is of a sufficient size to perform its intended function but the structure is essentially the same regardless of size. It should be noted that the assembly 10 may be implanted for various therapeutic uses, and may also be used for non-biological applications, with slight modifications. An essential element of the assembly 10 is a bladder 20 which responds to the surrounding environment, without requiring a source of power. The present invention as shown in FIGS. 1 14 is primarily concerned with relieving IOP, and various aspects of its structure are specifically adapted for use in a human eye. In one aspect of the invention for example, the size of the bladder 20 may be selected in accordance with the amount of IOP to be relieved, as will be explained in more detail later.

Figure 2A:
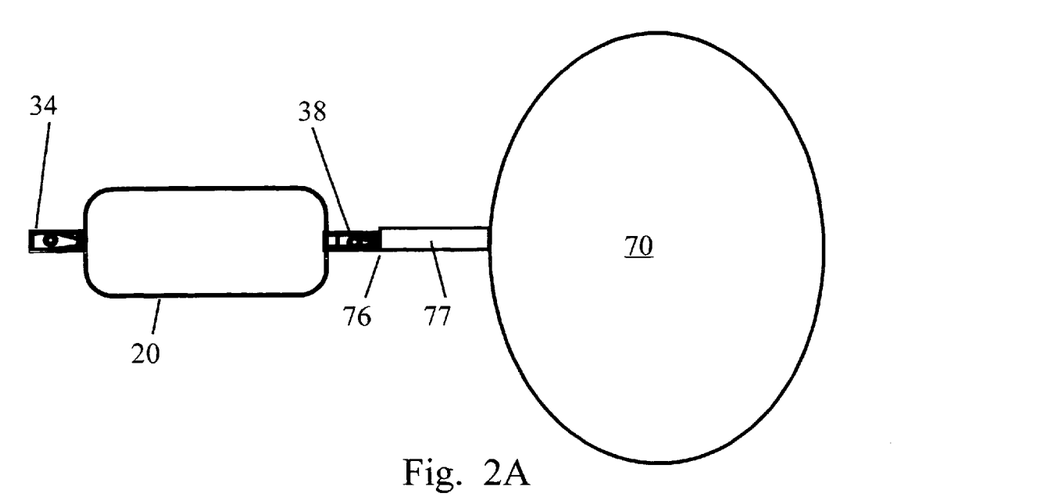
FIG. 2A is a plan view, partly in section, of the pump assembly of the present invention.
Figure 2B:
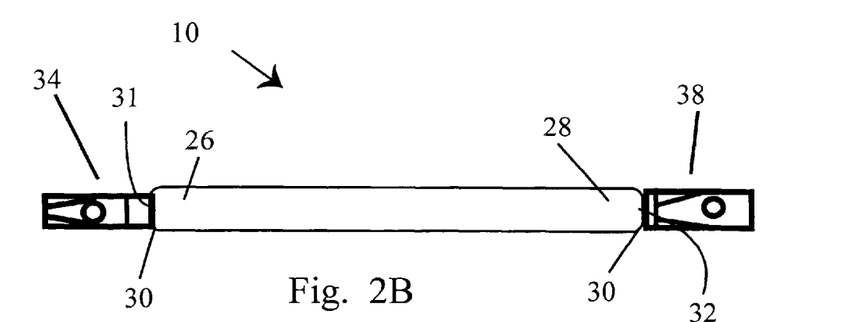
FIG. 2B is a side elevational view, partly in section, showing the bladder and the one-way check valves of the pump assembly in the quiescent state.

The primary actuator of the assembly 10 is the bladder 20, the sidewalls 22 of the bladder shown in the non-deflected, quiescent state in FIG. 2B. In accordance with a preferred embodiment of the invention, the bladder 20 is made from an elastic material capable of repeated expansion and contraction without permanent deformation. An elastic polymeric material may be used for this application. The minimum amount of force required to cause inward or outward deflection of the bladder sidewalls 22, which may be of the order of a few grams, is a function of the type and thickness of the elastic material employed, and is chosen in accordance with the anticipated deployment of the pump assembly 10, or, more particularly, the disease state or IOP of the eye into which the assembly 10 is implanted. The amount of fluid displaced by the bladder 20 is function of the bladder volume, and thus the ability of the apparatus to relieve pressure is a function of bladder volume and sidewall 22 thickness and flexibility. This additional drainage caused by the pumping action of the apparatus may be tailored to exactly match the deficiency in draining the aqueous humor out of the anterior chamber for glaucoma patients as will be described in more detail below.

For example, in the case of an ocular implant to treat glaucoma, sidewall 22 deflection should occur at a pressure slightly above, or below, normal pressure for the eye. For example, for a typical bladder volume of 10 mm$^3$, and assuming mild random environmental energy, drainage of about 1 microliter per minute is anticipated. As such, the pump 10 is essentially self regulating, the thickness, and therefore the pressure sensitivity, of the sidewalls 22 being determined using methods as would be apparent to one of ordinary skill in the art. Thus, for example, in the event the IOP rises above normal eye pressure, the sidewalls 22 will be deflected inward causing aqueous humor to be expelled outward via a drainage conduit as will be explained in more detail later. The amount of inward deflection of the sidewalls 22 will be directly proportional to the ambient pressure in the implant area, as will be the amount of fluid displaced. Also, the volume of the bladder 20 is chosen in accordance with the desired functionality and local environment, as would also be apparent to one of skill in the art. For example, an individual with very high IOP might require a slightly larger pump volume, to allow for the removal of more fluid. Also, the hardness of the pump sidewalls 22 may be slightly increased to limit deflection in the event of implantation in a high pressure environment, as the sidewalls 22 would have to be sufficiently resilient to allow for periodic return to a non-deflected or even expanded state. Some experimentation may be required to find the pump volume and resiliency for a particular application. In the embodiment shown in FIGS. 2A-8 the assembly 10 includes a bladder 20 which is slightly expanded in its non-flexed state.

The bladder 20 is defined by mutually opposed end portions, anterior end 26, and posterior end 28, sidewalls 22, and edge regions 30, providing an essentially seamless construction. Edge regions 30 and end portions 26, 28 may be rigid relative to sidewalls to ensure shape retention. Openings 30, 32 formed in end portions 26, 28 allow for fluid flow into and through an inlet or intake conduit 34 which is affixed within opening 30 in fluid tight relation thereto at one end, and open at the other end. into the interior of the bladder 20, which serves as a pumping chamber 36, and out through discharge conduit 38 which is secured in fluid tight relation within end portion 28. A one way check valve 40 includes stop partition 42 having an aperture 43 formed therein, and spherical plug member 44 sized to selectively block fluid flow through the aperture 43, the combination serving to selectively permit fluid flow into the conduit 34. Discharge or drainage conduit 38 includes check valve 48 which includes stop partition 50 having an aperture 52 formed therein, and spherical plug member 54 sized to selectively block fluid flow through the aperture 55, the combination serving to selectively permit fluid flow into and through the conduit 38. It can be readily appreciated that without check valves 40, 48 fluid would flow out of the pumping chamber 36 in both directions when the sidewalls 22 are contracted, and fluid would be drawn into the chamber 36 from opposite directions when the sidewalls 22 are expanded. Thus the apparatus 10 is designed to allow fluid to flow, from one direction, via conduit 34 into the pumping chamber 36, while also allowing unidirectional fluid flow from the chamber via conduit 38. The bladder 20, conduits 34, 38, and all other components of the assembly made from a biocompatible material such as medical grade silicone rubber. The methods of forming resilient devices made of rubber or plastic, including regions having relative hardness are well known in the art and do not constitute a part of the invention.

Figure 3:
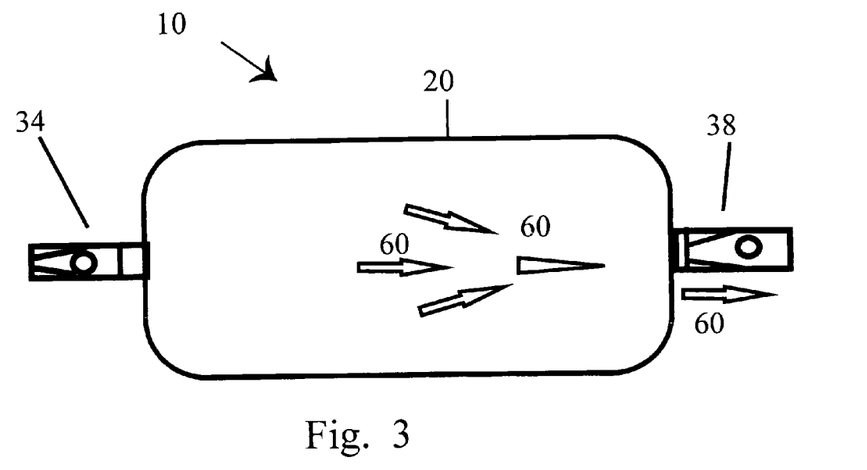
FIG. 3 is a plan view, partly in section, of the bladder of the pump assembly of the present invention showing inward deflection of the bladder and the resultant fluid flow.
Figure 4:
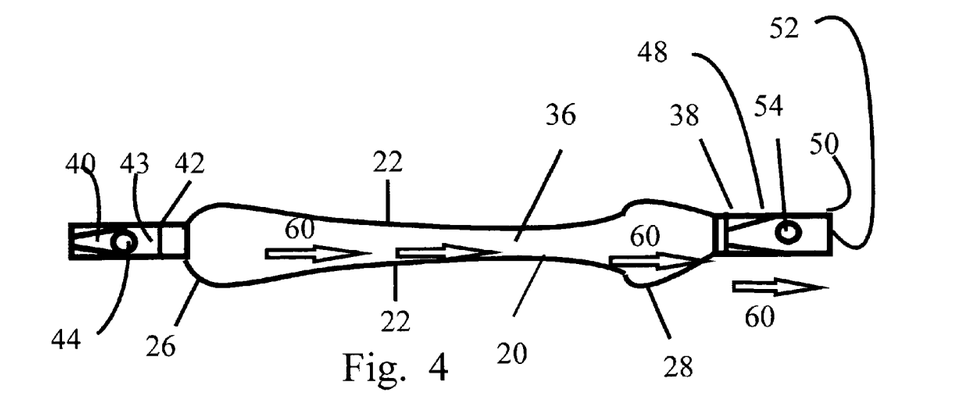
FIG. 4 is a side elevational view, partly in section, of the bladder also showing inward deflection of the pump bladder and the resultant fluid flow.
Figure 5:
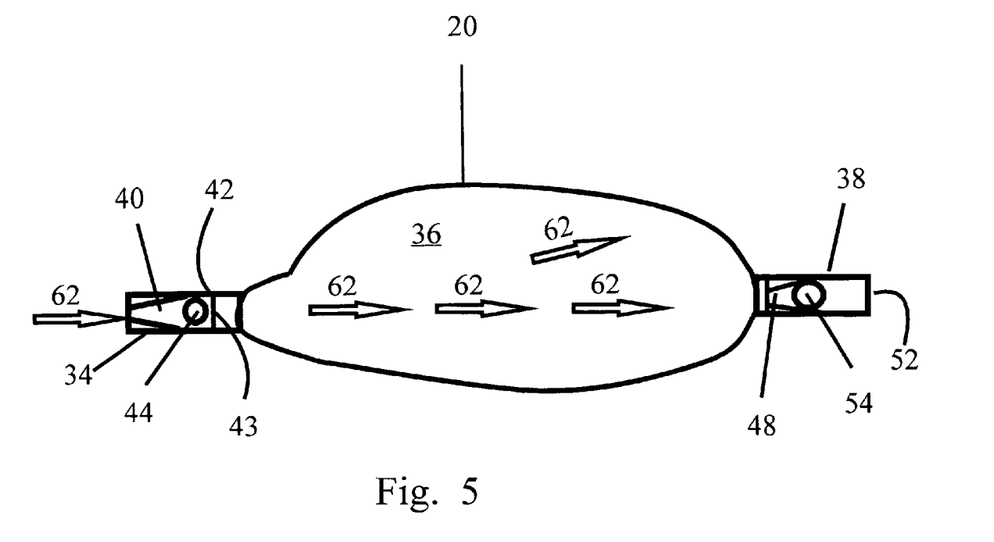
FIG. 5 is a side elevational view, partly in section, of the bladder showing outward expansion of the bladder and the resultant inward fluid flow.

Operation of the flexible bladder actuator 20 of the assembly 10 may be described generally as follows. Once situated for deployment within, e.g., an implant area, for example, right above the iris 9 on the sclera 1 underneath the eyelid, the bladder 20, in response to the local random pressure due to eye movement and other environmental dynamics, will remain relatively unaffected provided the ambient pressure is within a predetermined range, as shown in FIG. 2B. As is well known by those of skill in the art, the random motion of the eye is continuous, and slight pressure fluctuations are constant. In the case of an ocular implant, the range of nominal pressure would be the normal pressure range for a normal human eye. If the ambient pressure is above the predetermined range, the bladder sidewalls 22, with the appropriate thickness and flexibility as discussed above, will become inwardly deflected as shown in FIGS. 3 and 4. Fluid will flow as indicated by arrows 60 from the bladder 20 into and through discharge conduit 38 to the distribution plate 70. Discharge conduit 38 may be connected to an additional conduit (not shown) to pump fluid away from the implant area to the back of the eye and over the distribution plate 70. Note that the combination of conduit 77 and distribution plate 70, in a way, act like the traditional valves such as the Ahmed valve (U.S. Pat. No. 5,785,674), Baerveldt (U.S. Pat. No. 5,476,445), Krupin (U.S. Pat. No. 5,454,796), or Molteno (U.S. Pat. No. 4,570,901). However, these valves are passive shunts and create a scar tissue bleb which forms around the assembly, often occluding the opening of the drainage conduit and rendering the device non-functional. The present invention provides an active continuously pumping aqueous humor and is thus unlikely to allow any bleb to form. The discharge conduit 38 may also include a widened end portion (not shown) to disperse the effluent material. When the ambient pressure decreases or momentarily fluctuates, the bladder sidewalls 22 expand, returning to their original shape by way of stored resilient energy, this causes fluid to be drawn into the bladder or pumping chamber 36 via check valve 40, and conduit 34, as shown in FIG. 5, arrows 62. As the local pressure continues to fluctuate due to eye movement, the bladder 20 will alternate between the expanded and contracted or compressed state, alternately taking in and expelling fluid from the chamber 36. The random and constant motion of the eye will cause constant deflections of the sidewalls 22, which will tend to return to a state of deflection or expansion reflective of the local pressure conditions. It is the constant motion of the eye causing constant motion of the bladder sidewalls 22 which provides power for the assembly 10, with the resilient action of the sidewalls 22 constantly reforming to a shape consistent with the ambient pressure causing continuous pumping action when high or low pressure is present. If the local pressure becomes normal, as may be the case for a glaucoma patient taking medication to control IOP, random eye motion will cause only minimal pumping action, so that normal eye pressure is maintained. If the pressure is high relative to the flexibility of the sidewalls 22, random eye motion will cause continuous discharge of fluid, as the sidewalls 22 will be in a nearly constant state of inward deflection, interrupted briefly by the eye motion which will tend to deform and cause temporary expansion of the sidewalls 22, allowing for the intake of the aqueous humor which must be drained from the anterior chamber in order to relieve ocular pressure. Finally, if the local ambient pressure is low, sidewalls will be biased in an expanded condition as shown in Fig. Of course, patients would be monitored to determine if their ocular pressure has increased or decreased over time, with adjustments made to the assembly 10, or removal thereof, as may be required. The adjustment would involve adjusting the volume and flexibility of the bladder 20 as discussed above, to a volume and flexibility consistent with the observed ocular pressure.

Figure 6:
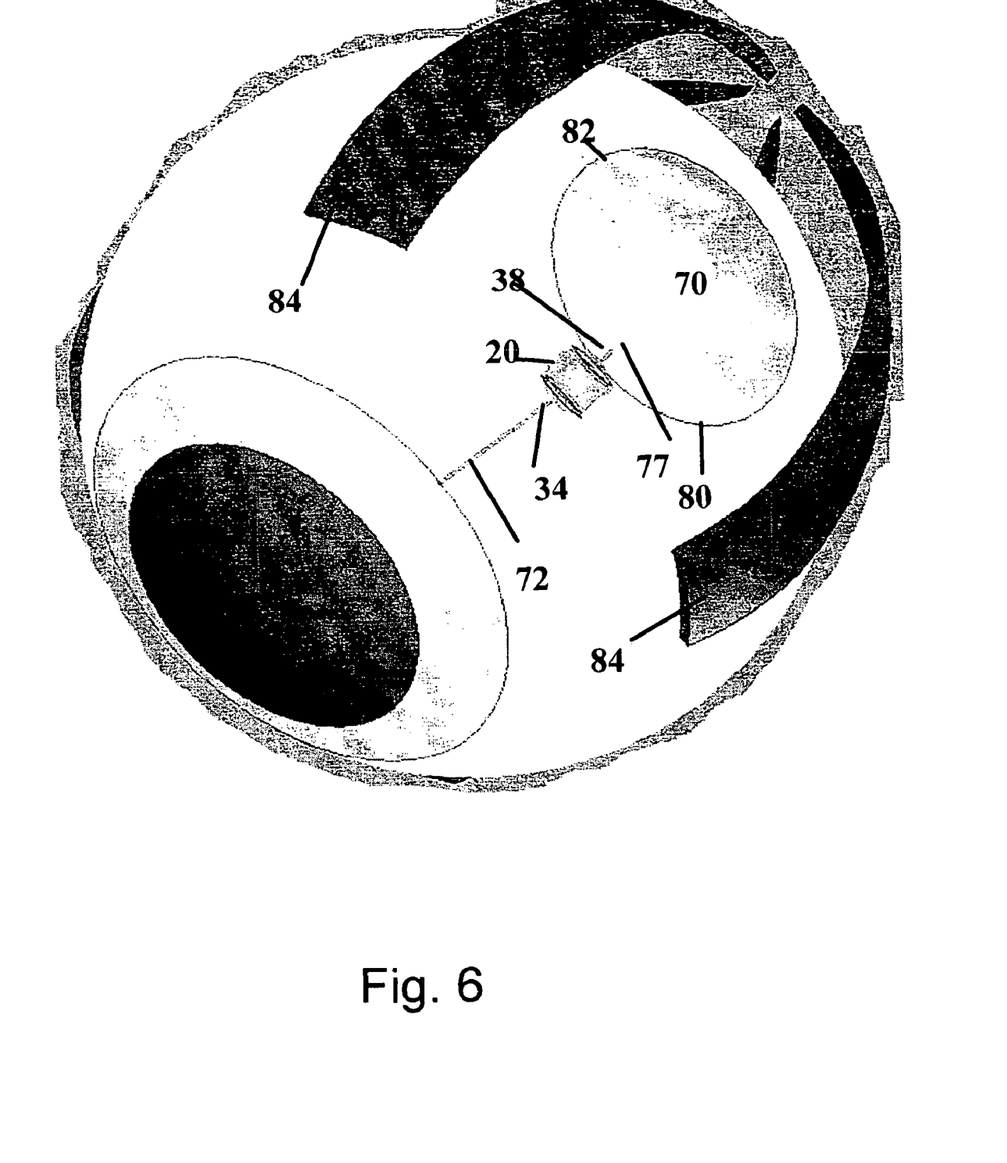
FIG. 6 is a perspective view of the pump assembly of the present invention implanted in a human eye and positioned to relieve IOP.
Figure 7:
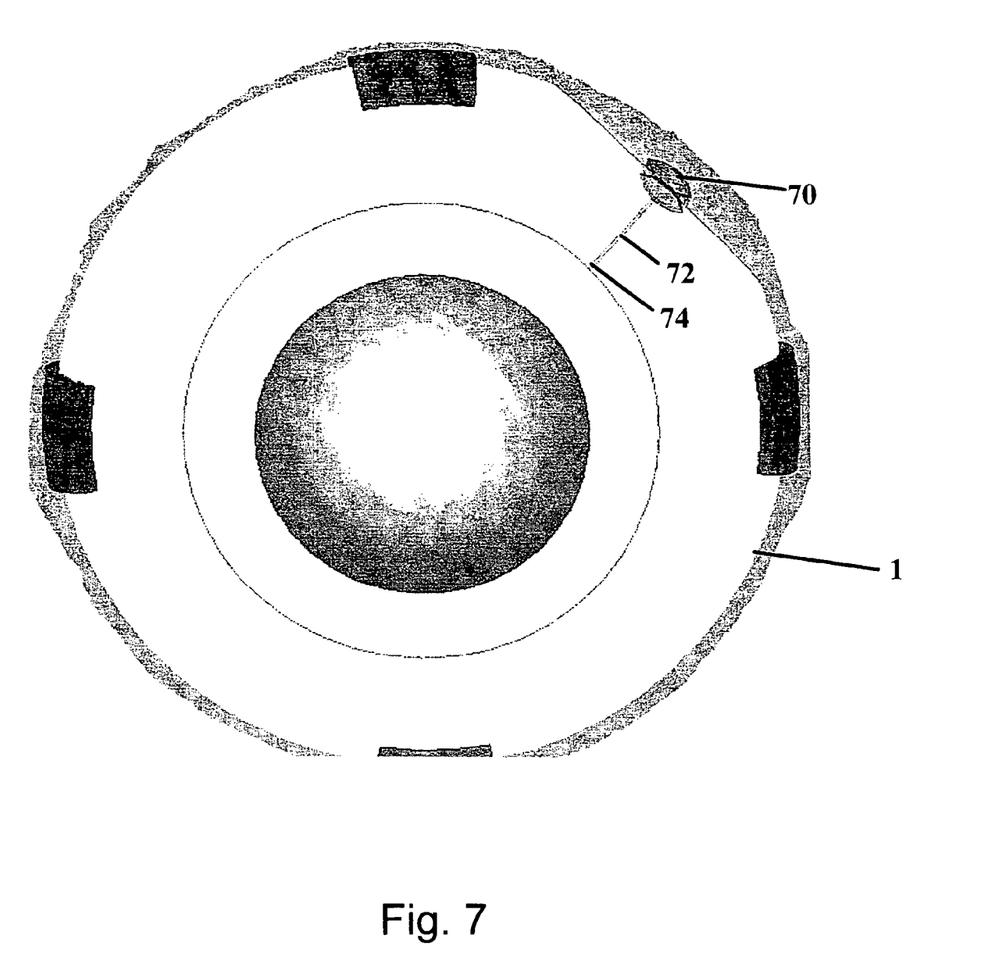
FIG. 7 is a front elevational view of the pump assembly of the present invention implanted in a human eye and positioned to relieve IOP.
Figure 8:
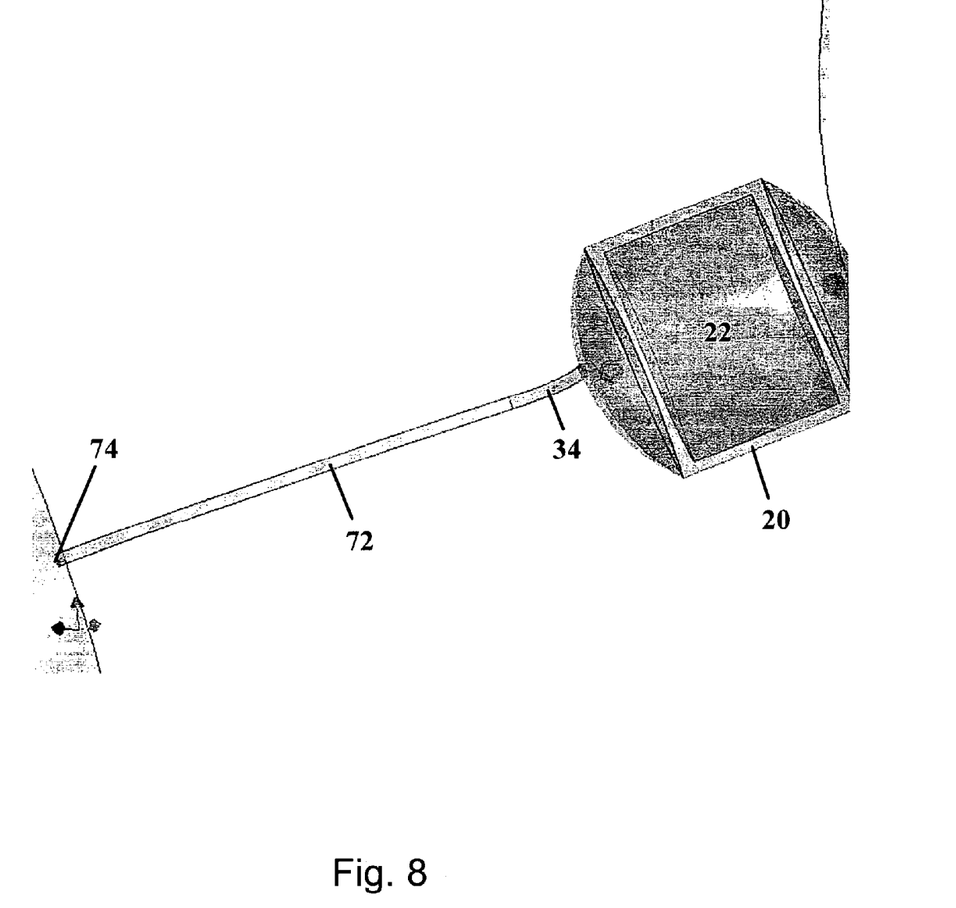
FIG. 8 is a detail of the implanted pump assembly of the present invention as shown in FIGS. 6 and 7, illustrating the position of the influent and effluent conduits with respect to the anterior chamber of the eye.

A key aspect of the invention is the use of a distribution plate 70 for dispersing fluid flowing from discharge conduit 38. As can be seen especially in FIGS. 6-8, intake conduit 34 may be extended by a length of flexible tubing 72, the tubing having an opening 74 positioned in the anterior chamber 12 of the eye 1. The distribution plate 70 is positioned proximate the opening 76 of the discharge conduit, and is preferably attached directly to the bladder 20, the conduit 38, or an extension of flexible tubing 77 fluidically coupled thereto, in such a way as to avoid interfering with the normal expansion and contraction of the sidewalls 22 of the bladder. The plate 70 may be fabricated from a similar, but relatively harder, material as the bladder 20, and attached thereto by adhesive, heat fusion or other suitable means. For example, the plate 70 can be attached proximate the end portion 28 of the bladder 20. Alternatively, the plate 70 and bladder 20 may be sutured in position on the sclera so that the plate 70 can effectively disperse aqueous humor discharged from conduit 38. All of the components of the assembly 10 may be sutured in position on the sclera 1 as shown in FIGS. 6-8, the end portions 80, 82 of the plate 70 secured beneath the check ligaments 84, with the bladder positioned under the eyelid.

As described above, local dynamic variations of the pressure, combined with motion of the eye cause the elastic bladder 20 of the implanted pump to go through cycles of compression and expansion and thus pump the aqueous humor out of the anterior chamber of the eye out to the plate 70 to evenly distribute the aqueous humor. The apparatus can be used for other medical application such as the treatment of hydrocephalus to drain fluid from a swollen brain or can be used to administer drugs, with the random dynamic motion of the body at the implantation site used to power the pump in the manner described above.

An alternative embodiment of the assembly, indicated by the numeral 100, and shown in FIGS. 9-12, combines the bladder 102 and distribution plate into a single component. The bladder 102 has a substantially oval shape as does the plate in the previous embodiment, with an arcuate cross-section as can be seen FIG. 10. The edge regions 104 of the bladder 102 may be slightly hardened to maintain the arcuate cross sectional shape, especially the laterally disposed wings 106 which are adapted for positioning beneath the extraocular muscles 110 as is illustrated diagrammatically in FIGS. 12 and 13. The combined bladder and plate 102 is functionally similar to the previous embodiment, with intake 112 and discharge 114 conduits integrally formed and positioned as shown.

Figure 9:
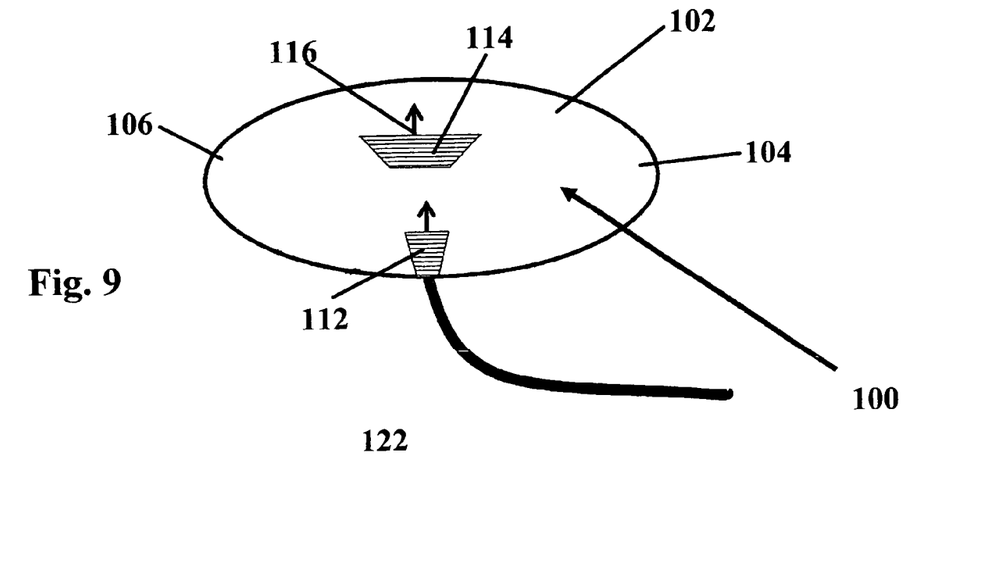
FIG. 9 is a plan view, partly in section, of an alternative embodiment of the bladder pump assembly.
Figure 10:
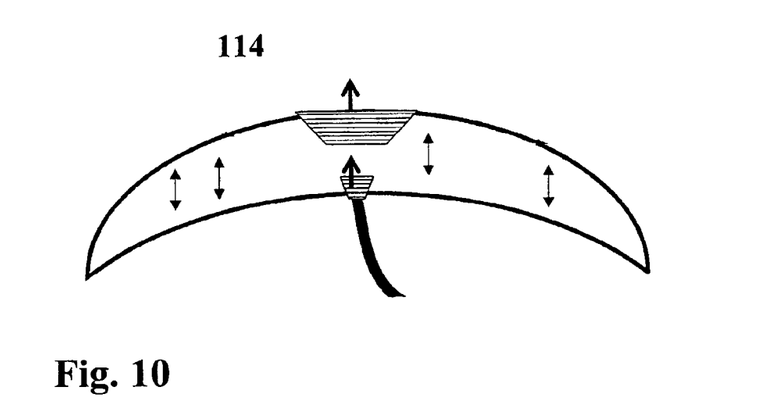
FIG. 10 is a side elevational view, partly in section, of the bladder pump of FIG. 9.

Specifically, the intake conduit 112 is positioned approximately centrally of the wings 106 in the edge region 104 of the bladder, while the discharge conduit 114 is axially aligned with the intake conduit 112 but positioned inwardly of the edge region 104 so that the opening 116 of the conduit, which is preferably flared, is placed to allow dispersion of aqueous humor over the outer surface of the upper sidewall 118 of the bladder 102, the upper sidewall 118 essentially performing the same function as the plate 70 in the previous embodiment. Both the upper 120 and lower 118 sidewalls are flexible to allow for deformation as discussed above, to create the pumping action. Alternatively, the lower contact surface area or underside 121 of the bladder lower sidewall 118 may be relatively rigid, and contoured to match the curvature of the eye, while the upper surface 111 is resilient and flexible as in the previous embodiment. A length of flexible tubing 122 is fluidically coupled to intake 112, the open end 124 of the tubing 122 positioned in the anterior chamber 12 of the eye.

Figure 11:
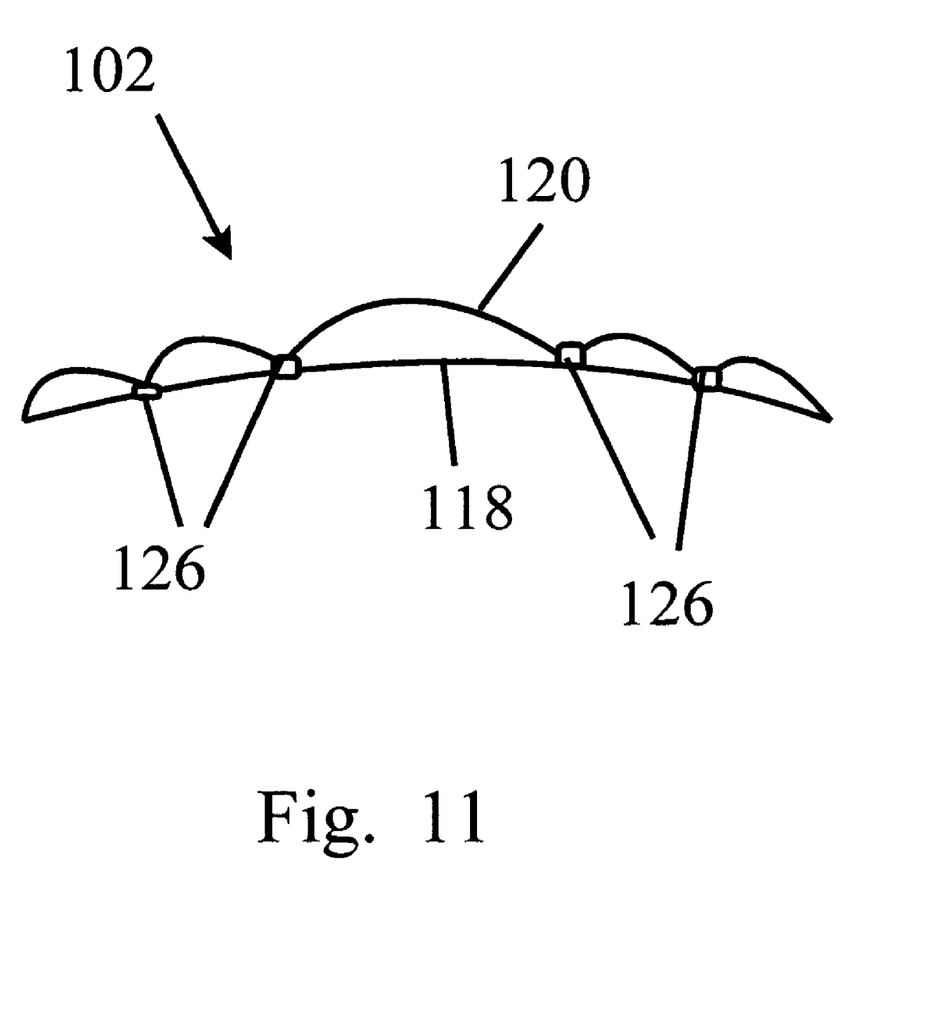
FIG. 11 is a cross section of the bladder wall illustrating the use of sealed apertures for limiting expansion of the bladder.
Figure 12:
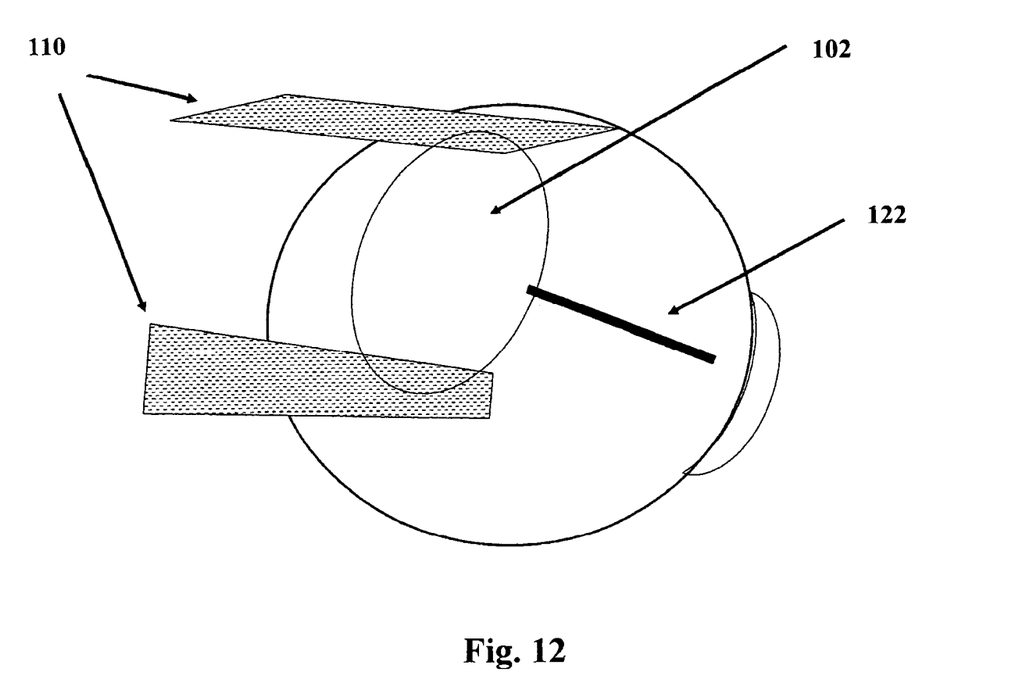
FIG. 12 is a schematic illustration of the assembly of FIGS. 9 and 10 implanted in a human eye, detailing the position of the assembly relative to the various parts of the eye.

When implanting a bladder or other movable apparatus into a human eye, care must be taken to limit the expansion or movement of the apparatus to avoid injuring the muscles, ligaments, or other eye tissue. To that end, expansion of the bladder 102 may be limited by fusing upper 120 and lower 118 sidewalls at a plurality of discrete points 126 as shown in FIG. 11. The fused areas 126 are formed in groups of two on opposite sides of the axis between intake 112 and discharge 114 conduits, each set of fused areas 126 evenly spaced from the axis. In lieu of the fused areas 126, a series of annular regions of compressed or relatively hard material may be formed along opposing edges of the bladder. As with the above embodiment, any of several well known methods for fabricating plastic or rubber components of unitary construction having areas of relative hardness, or shaped perturbations or the like may be used.

Figure 13:
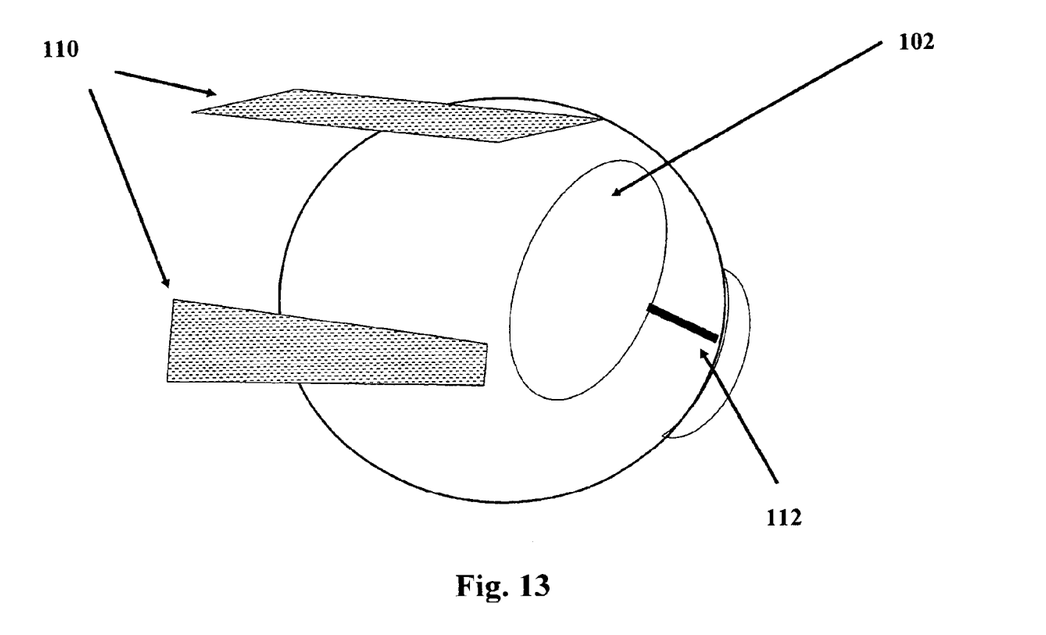
FIG. 13 is a schematic illustration of the assembly of FIGS. 9 and 10 implanted in a human eye, showing an alternate positioning for the assembly.
Figure 14:
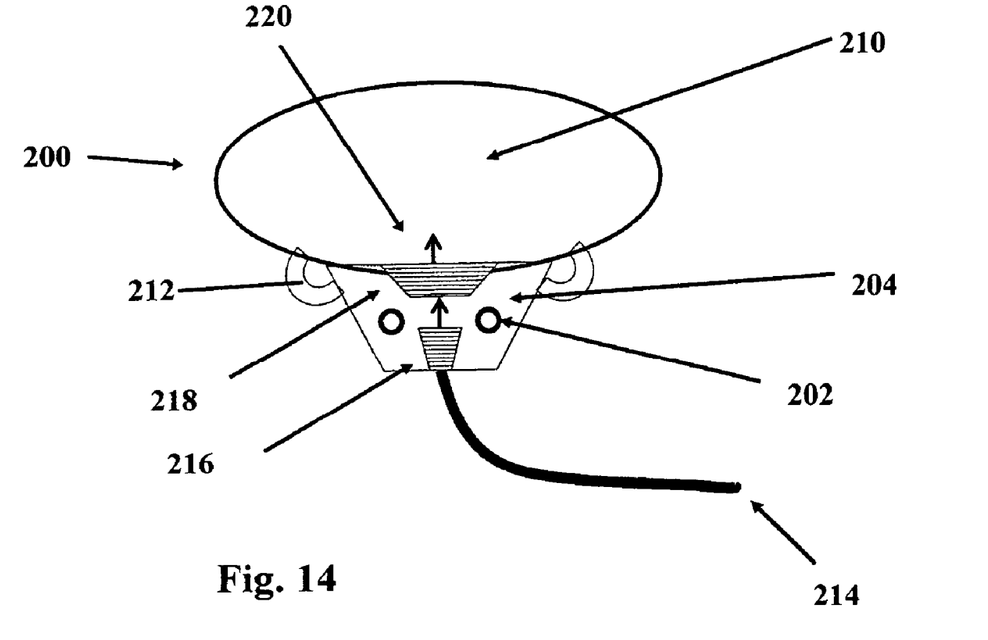
FIG. 14 is a schematic illustrating fluid flow of the pump assembly as configured in the embodiment shown in FIGS. 2A-8.

FIG. 13 shows schematically an alternative placement for the bladder 102 of the assembly. With this placement, the bladder plate 102 is positioned closer to the anterior chamber 12, between the check ligaments.

FIG. 14 illustrates a pump assembly 200 essentially identical to the pump assembly 10 discussed above, with the exception that an expansion limiting means, indicated by reference numeral 202, has been incorporated into the bladder 204 of the assembly. It can be seen that the expansion limiting means 202 is essentially a series of hardened or compressed annular regions positioned lengthwise across the side of the bladder 204 as discussed above with respect to the previous embodiment 100. Any of several well known techniques may be used for forming these regions, as also discussed above. The assemblies 10, 200 may be connected to the drainage plate 70, 210, by relatively rigid connecting members 212, made of the same material as the drainage plate 210. Assembly 200 also has an intake conduit 214, check valves, 216, 218, and a discharge conduit 220 as in the previous embodiments, and is functionally identical thereto.

As in the above, the entire assembly 100, 200 is sutured into position. Note that basically the same surgical procedure used to implant the existing glaucoma valves such as those discussed in the Ahmed, Baerveldt, Krupin or Molteno references will be used to implant the various embodiments of the present bladder pump and plate combination assembly in the eye of a patient, said procedures herein incorporated by reference.

It is to be understood that the provided illustrative examples are by no means exhaustive of the many possible uses for our invention.

From the foregoing description, one skilled in the art can easily ascertain the essential characteristics of this invention and, without departing from the spirit and scope thereof, can make various changes and modifications of the invention to adapt it to various usages and conditions.

It is to be understood that the present invention is not limited to the sole embodiment described above, but encompasses any and all embodiments within the scope of the following claims:

What is claimed is:

1. A pump assembly for implantation into an anterior chamber of a human eye for controlling ocular pressure comprising:
   a main body with a unitary construction and formed of an elastic material into an elastic bladder, having an anterior end, a posterior end, and an interior chamber;
   an intake conduit having an open end, and an opposing end of said intake conduit fluidly coupled to said anterior end;
   an outlet conduit having an open end, and an opposing end fluidly coupled to said interior chamber at one end;
   a first valve means for selectively allowing fluid flow from said intake conduit to said interior chamber, a second valve means for selectively allowing fluid flow from said interior chamber into and through said drainage conduit;
   fluid displacement means for causing fluid flow through said main body, said fluid displacement means including said elastic bladder having elastic sidewalls biased in an expanded state where elasticity of said elastic bladder sidewalls is varied in accordance with a measured ocular pressure in said anterior chamber;
   whereby said elastic sidewalls are constructed and configured such that external pressure fluctuations cause deflection and/or expansion of said elastic sidewalls harvesting energy from an implantation environment and using said energy to continuously pump fluid out of the anterior chamber.

2. The pump assembly of claim 1 wherein said main body, said intake conduit, said discharge conduit, and said distribution plate are made of a biocompatible material.

3. The pump assembly of claim 1 wherein said main body, said intake conduit, said discharge conduit, and said distribution plate are made of medical grade silicone rubber.

4. The pump assembly of claim 1 wherein said assembly is implanted in a human head to address hydrocephalus and the self-powered drainage of excess liquid from a swollen brain which has experienced trauma, said assembly further excluding a fluid distribution plate.

5. The pump assembly of claim 1 wherein said assembly is implanted anywhere in a human or animal body for self-powered drug delivery, said assembly further comprising a drug reservoir positioned proximate to said bladder pump.

* * * * *